United States Patent
Pinsonneault

(10) Patent No.: US 8,036,918 B1
(45) Date of Patent: Oct. 11, 2011

(54) SYSTEMS AND METHODS FOR CONVERSIONS OF DENIED TRANSACTIONS THROUGH PATIENT FUNDING

(75) Inventor: Roger Pinsonneault, Alpharetta, GA (US)

(73) Assignee: McKesson Financial Holdings Ltd., Hamilton (BM)

( * ) Notice: Subject to any disclaimer, the term of this patent is extended or adjusted under 35 U.S.C. 154(b) by 413 days.

(21) Appl. No.: 12/140,015

(22) Filed: Jun. 16, 2008

(51) Int. Cl.
*G06Q 10/00* (2006.01)

(52) U.S. Cl. ..................................... 705/3; 705/2; 705/4

(58) Field of Classification Search ................. 705/2–4; 600/300–301
See application file for complete search history.

(56) References Cited

U.S. PATENT DOCUMENTS

| | | | |
|---|---|---|---|
| 5,628,530 A | 5/1997 | Thornton | |
| 6,012,035 A | 1/2000 | Freeman et al. | |
| 6,726,092 B2 * | 4/2004 | Goldberg et al. | 235/375 |
| 6,757,898 B1 | 6/2004 | Ilsen et al. | |
| 6,769,228 B1 | 8/2004 | Mahar | |
| 7,155,397 B2 | 12/2006 | Alexander et al. | |
| 7,337,129 B1 | 2/2008 | Lowry et al. | |
| 2002/0002495 A1 | 1/2002 | Ullman | |
| 2002/0087583 A1 | 7/2002 | Morgan et al. | |
| 2002/0111832 A1 | 8/2002 | Judge | |
| 2002/0198831 A1 | 12/2002 | Patricelli et al. | |
| 2003/0009367 A1 | 1/2003 | Morrison | |
| 2003/0050799 A1 | 3/2003 | Jay et al. | |
| 2003/0074234 A1 | 4/2003 | Stasny | |
| 2003/0105711 A1 * | 6/2003 | O'Neil | 705/39 |
| 2003/0149625 A1 | 8/2003 | Leonardi et al. | |
| 2003/0154163 A1 | 8/2003 | Phillips et al. | |
| 2003/0229540 A1 | 12/2003 | Algiene | |
| 2004/0039599 A1 | 2/2004 | Fralic | |
| 2004/0073456 A1 * | 4/2004 | Gottlieb et al. | 705/2 |
| 2004/0073457 A1 | 4/2004 | Kalies | |
| 2004/0078234 A1 | 4/2004 | Joseph, Jr. | |
| 2004/0117323 A1 | 6/2004 | Mindala | |
| 2004/0148198 A1 | 7/2004 | Kalies | |
| 2004/0153336 A1 | 8/2004 | Virdee et al. | |
| 2004/0236630 A1 | 11/2004 | Kost et al. | |
| 2004/0249745 A1 | 12/2004 | Baaren | |

(Continued)

FOREIGN PATENT DOCUMENTS

CA 2482370 3/2006
(Continued)

OTHER PUBLICATIONS

"Pharmaceutical Manufacturer Assistance Programs" by Marie Chisholm et al,; Arch Intern Med., vol. 162, published Apr. 8, 2002.*

(Continued)

*Primary Examiner* — Vivek Koppikar
(74) *Attorney, Agent, or Firm* — Sutherland Asbill & Brennan LLP

(57) ABSTRACT

Systems and methods may be provided for claim denial conversion. The systems and methods may include receiving a prescription claim from a pharmacy, where the prescription claim is associated with a drug or other product requested by a customer, routing the prescription claim to a claims processor for adjudication, and receiving, from the claims processor, a denied claim response for the claim request. The systems and methods may further include determining that funding is available to cover at least a portion of a price of the requested drug or other product, converting the denied claim response to an approved claim response upon determination of the available funding, and transmitting the approved claim response to the pharmacy.

20 Claims, 4 Drawing Sheets

U.S. PATENT DOCUMENTS

| | | | |
|---|---|---|---|
| 2005/0015280 A1 | 1/2005 | Gabel et al. | |
| 2005/0060201 A1 | 3/2005 | Connely et al. | |
| 2005/0102169 A1 | 5/2005 | Wilson | |
| 2005/0154627 A1 | 7/2005 | Zuzek et al. | |
| 2005/0187793 A1 | 8/2005 | Myles | |
| 2005/0197862 A1 | 9/2005 | Paterson et al. | |
| 2005/0240473 A1 | 10/2005 | Ayers | |
| 2005/0288972 A1 | 12/2005 | Marvin et al. | |
| 2006/0020514 A1 | 1/2006 | Yered | |
| 2006/0026041 A1 | 2/2006 | Ullman et al. | |
| 2006/0149595 A1 | 7/2006 | Williams et al. | |
| 2006/0149784 A1 | 7/2006 | Tholl et al. | |
| 2006/0184391 A1 | 8/2006 | Barre et al. | |
| 2006/0259363 A1 | 11/2006 | Jhetam | |
| 2007/0005402 A1 | 1/2007 | Kennedy et al. | |
| 2007/0050209 A1 | 3/2007 | Yered | |
| 2007/0136100 A1 | 6/2007 | Daugherty et al. | |
| 2007/0185799 A1* | 8/2007 | Harrison et al. | 705/36 T |
| 2007/0233525 A1 | 10/2007 | Boyle | |
| 2007/0233526 A1 | 10/2007 | Hoffman et al. | |
| 2007/0239493 A1 | 10/2007 | Sweetland et al. | |
| 2009/0287558 A1 | 11/2009 | Seth et al. | |

FOREIGN PATENT DOCUMENTS

| | | |
|---|---|---|
| WO | 9503569 | 2/1995 |
| WO | 0039737 | 7/2000 |
| WO | 2007025295 | 3/2007 |

OTHER PUBLICATIONS

Sampson, R.J., Taking Control of Health Care Costs, Best's Review—Life Health Insurance Edition, Nov. 1983, pp. 64-66, vol. 84, Issue 7, USA.

Anonymous, ACS to Demonstrate Electronic Health Record Solution Suite at MMIS 2007 Conference; EHR Tools Consolidate Data, Provide Useful Information at the Point of Care for Medicaid Providers, Payers, and Patients, PR Newswire, Aug. 13, 2007, New York, NY, USA.

Lamb, J., New Era of Electronic Medicine Management: E-Prescriptions, Britain's Traditionally Cautious National Health Service is Starting Trials for Online Prescription, with the Aim of Cutting Costs. Financial Times, London, Feb. 21, 2001, p. 6, London, United Kingdom.

Anonymous, Pharmacy Industry Leaders Launch Firm to Supply Real-Time Data. PR Newswire. Jul. 30, 2001, p. 1, New York, NY, USA.

Anonymous, Medic: On-line Goes In-House, Chain Store Age Executive, Jan. 1987, pp. 128-132. vol. 63, Issue 1, USA.

Anonymous, TechRx Announces Successful Beta Deployment of T-Rex. PR Newswire. May 13, 2002.

www.ncoil.org/news/DrugCards2.doc dated Apr. 2002.

Non-final Office Action for U.S. Appl. No. 12/189,654 mailed Jan. 22, 2010.

Non-final Office Action for U.S. Appl. No. 12/189,650 mailed Jan. 22, 2010.

Notice of Allowance for U.S. Appl. No. 12/189,650 mailed Aug. 13, 2010.

Notice of Allowance for U.S. Appl. No. 12/165,221 mailed Nov. 16, 2010.

Non-Final Office Action for U.S. Appl. No. 12/956,411 mailed Jan. 24, 2011.

Non-Final Office Action for U.S. Appl. No. 12/415,062 mailed Mar. 30, 2011.

Notice of Allowance for U.S. Appl. No. 11/674,069 dated Jul. 19, 2010.

* cited by examiner

SYSTEMS AND METHODS FOR CONVERSIONS OF DENIED TRANSACTIONS THROUGH PATIENT FUNDING

FIELD OF THE INVENTION

Aspects of the invention relate generally to prescription claims, and more particularly, to system and method for converting a denied prescription claim to an approved prescription claim.

BACKGROUND OF THE INVENTION

Pharmaceutical manufacturers spend a significant amount of effort, time, and/or money promoting the advantages of their prescription products (e.g., drugs, medical equipment, etc.) against those of competing products. Indeed, pharmaceutical manufacturers promote their prescription products to influence the prescription writing activity of physicians or other healthcare providers. However, prescriptions claims may be denied by a claims processor, thereby thwarting the promotional efforts of pharmaceutical manufacturers. If a prescription claim is denied, a patient may decide to not accept the full financial burden of a prescription product either by not filling the prescription or otherwise by not utilizing the prescription product to the full extent prescribed by the physician. Accordingly, there is a need to intercept denied claim responses from claim processors and provide financial funding in order to convert denied claims to approved claims.

SUMMARY OF THE INVENTION

Example embodiments of the invention may be directed to intercepting a denied claim from a claims processor for conversion to an approved claim. Embodiments of the invention may include one or more of the following: receiving a prescription claim from a pharmacy, routing the prescription claim to a claims processor, receiving a denial of the prescription claim (e.g., a denied claim), recognizing the denial and the availability of funding by a pharmaceutical manufacturer or other entity, determining the extent to which funding is available, converting the denied response to an approved response, and performing financial processing to allocate the funding to a pharmacy in accordance with the coversion of the denied response to an approved response.

According to an example embodiment of the invention, there may be a computer-implemented method for claim denial conversion. The method may include receiving a prescription claim from a pharmacy, where the prescription claim is associated with a product (e.g., drug, durable medical equipment (DME) product, etc.) requested by a customer, routing the prescription claim to a claims processor for adjudication, and receiving, from the claims processor, a denied claim response for the claim request. The method may also include determining that funding is available to cover at least a portion of a price of the requested product, converting the denied claim response to an approved claim response upon determination of the available funding, and transmitting the approved claim response to the pharmacy.

According to another example embodiment of the invention, there may be a system for claim denial conversion. The system may include a memory configured to store computer-executable instructions, and a processor in communication with the memory. The processor may be operable to execute the computer-executable instructions to receive a prescription claim from a pharmacy, where the prescription claim may be associated with a product requested by a customer, route the prescription claim to a claims processor for adjudication, and receive, from the claims processor, a denied claim response for the claim request. The process may also be operable to execute the computer-executable instructions to determine that funding is available to cover at least a portion of a price of the requested product, convert the denied claim response to an approved claim response upon determination of the available funding, and transmit the approved claim to the pharmacy.

BRIEF DESCRIPTION OF THE DRAWINGS

Reference will now be made to the accompanying drawings, which are not necessarily drawn to scale, and wherein.

DETAILED DESCRIPTION

Figure 1:
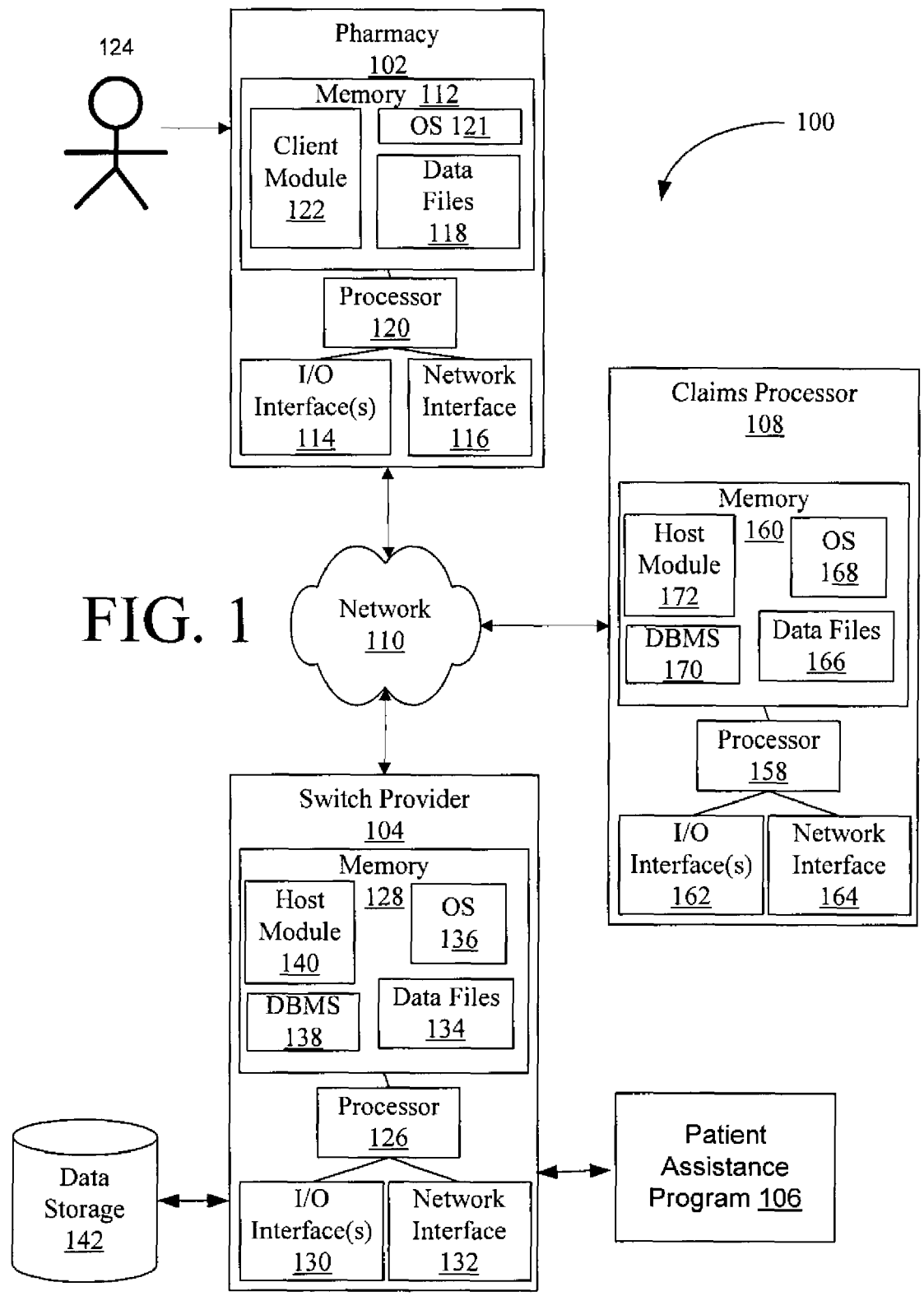
FIG. 1 illustrates an example system for converting a denied claim response to an approved claim response, according to an example embodiment of the invention.

Embodiments of the invention will be described more fully hereinafter with reference to the accompanying drawings, in which embodiments of the invention are shown. This invention may, however, be embodied in many different forms and should not be construed as limited to the embodiments set forth herein; rather, these embodiments are provided so that this disclosure will be thorough and complete, and will fully convey the scope of the invention to those skilled in the art. Like numbers refer to like elements throughout.

Embodiments of the invention are described below with reference to block diagrams and flowchart illustrations of systems, methods, apparatuses and computer program products. It will be understood that each block of the block diagrams and flowchart illustrations, and combinations of blocks in the block diagrams and flowchart illustrations, respectively, can be implemented by computer program instructions. These computer program instructions may be loaded onto a general purpose computer, special purpose computer such as a switch, or other programmable data processing apparatus to produce a machine, such that the instructions which execute on the computer or other programmable data processing apparatus create means for implementing the functions specified in the flowchart block or blocks.

These computer program instructions may also be stored in a computer-readable memory that can direct a computer or other programmable data processing apparatus to function in a particular manner, such that the instructions stored in the computer-readable memory produce an article of manufacture including instruction means that implement the function specified in the flowchart block or blocks. The computer program instructions may also be loaded onto a computer or other programmable data-processing apparatus to cause a series of operational elements or steps to be performed on the computer or other programmable apparatus to produce a computer-implemented process such that the instructions that execute on the computer or other programmable apparatus provide elements or steps for implementing the functions specified in the flowchart block or blocks.

Accordingly, blocks of the block diagrams and flowchart illustrations may support combinations of means for performing the specified functions, combinations of elements or steps for performing the specified functions, and program instruction means for performing the specified functions. It will also be understood that each block of the block diagrams and flowchart illustrations, and combinations of blocks in the block diagrams and flowchart illustrations, can be implemented by special purpose hardware-based computer systems that perform the specified functions, elements or steps, or combinations of special purpose hardware and computer instructions.

Embodiments of the invention can provide systems and methods by which denied claim responses from claim processors may be intercepted and converted to approved claim responses in accordance with a patient assistance program. In accordance with example embodiments of the invention, pharmaceuticals manufacturers, or representatives/providers associated therewith (collectively referred to as "pharmaceutical manufacturers"), or yet other entities, may provide for funding for the patient assistance program. According to an example embodiment of the invention, a marketplace for such denial conversions may include, but is not limited to, the funded marketplace, which includes insurers, pharmacy benefit managers (PBMs), third-party payors, etc.

Embodiments of the invention may include one or more of the following: receiving a prescription claim from a pharmacy, routing the prescription claim to a claims processor, receiving a denial of the prescription claim (e.g., a denied claim response), recognizing the denial and the availability of funding by a pharmaceutical manufacturer or other entity (e.g., licensee, distributor, etc.), determining the extent to which funding is available, converting the denied claim response to an approved claim response, and performing financial processing to allocate the funding to a pharmacy in accordance with the coversion of the denied claim response to an approved claim response. It will be appreciated that variations of the above-described embodiments are available as well. For example, a step of determining the extent to which funding is available may include forwarding the prescription claim information to a patient assistance program that evaluates the prescription claim for full or partial funding.

FIG. 1 illustrates an example system for converting a denied claim response to an approved claim response, according to an example embodiment of the invention. As shown in FIG. 1, a pharmacy 102, switch provider 104, and claims processor 108 may be in direct communication with each other or via a network 110, which as described below can include one or more private and public networks, whether wired or wireless, and which may include the Internet. Each of these components—the pharmacy 102, the switch provider 104, the claims processor 108, and the network 110—will now be discussed in turn. First, the pharmacy 102 may be any processor-driven device, such as a personal computer, laptop computer, handheld computer, and the like. In addition to having a processor 120, the pharmacy 102 may further include a memory 112, input/output ("I/O") interface(s) 114 and a network interface 116. The memory 112 may store data files 118 and various program modules, such as an operating system ("OS") 121 and a client module 122. The client module 122 may be an Internet browser or other software, including a dedicated program, for interacting with the switch provider 104. For example, a user 124, such as a consumer, pharmacist, or other pharmacy employee, may utilize the client module 122 in preparing and providing a prescription claim that is transmitted to the switch provider 104. Likewise, the pharmacy 102 may also utilize the client module 122 to receive data from the switch provider 104, including a response to the transmitted prescription claim.

Still referring to the pharmacy 102, the I/O interface(s) 114 may facilitate communication between the processor 120 and various I/O devices, such as a keyboard, mouse, printer, microphone, speaker, monitor, bar code readers/scanners, RFID readers, and the like. The network interface 116 may take any of a number of forms, such as a network interface card, a modem, a wireless network card, and the like. These and other components of the pharmacy 102 will be apparent to those of ordinary skill in the art and are therefore not discussed in more detail herein.

The switch provider 104 may include any processor-driven device that is configured for receiving, processing, and fulfilling requests from the pharmacy 102 related to pharmacy, benefits, and/or patient assistance transactions. The switch provider 104 may communicate with, or otherwise include, a patient assistance program module 106, which may operate to determine funding opportunities and provide funding for denied claims, as described herein. The switch provider 104 may therefore include a processor 126, a memory 128, input/output ("I/O") interface(s) 130, and a network interface 132. The memory 128 may store data files 134 and various program modules, such as an operating system ("OS") 136, a database management system ("DBMS") 138, and the host module 140. The host module 140 receives, processes, and responds to requests from the respective client module 122 of pharmacy 102, and further receives, processes, and responds to requests from the respective host modules 172 of the claims processor 108. Likewise, where the patient assistance program module 106 is provided separately from the switch provider 104, the host module 140 may transmit claim requests and/or responses to the claim requests to the patient assistance program module 106, and receive eligibility or funding information from the patient assistance program module 106. According to an example embodiment of the invention, the patient assistance program module 106 may include a processor and/or computer-executable instructions for implementing the methods described herein. For example, the patient assistance program module 106 may be operative to determine whether a claim is eligible for funding and if so, the extent to which funding is available.

The claims processor 108 may include any processor-driven device that is configured for receiving, processing, and fulfilling requests from the pharmacy 102 or switch provider 104 related to pharmacy and/or benefits transactions. The claims processor 108 may include a processor 158, a memory 160, input/output ("I/O") interface(s) 162, and a network interface 164. The memory 160 may store data files 166 and various program modules, such as an operating system ("OS") 168, a database management system ("DBMS") 170, and a host module 172. The host module 172 may receive, process, and respond to requests from the client module 122 of pharmacy 102, and may further receive, process, and respond to requests from the host module 140 of the switch provider 104. Those of ordinary skill in the art will appreciate that the claims processor 108 may include alternate and/or additional components, hardware or software without departing from example embodiments of the invention.

The network 110 may include any telecommunication and/or data network, whether public, private, or a combination thereof, including a local area network, a wide area network, an intranet, an internet, the Internet, intermediate hand-held data transfer devices, and/or any combination thereof and may be wired and/or wireless. The network 110 may also allow for real-time, off-line, and/or batch transactions to be transmitted between or among the pharmacy 102, the switch provider 104, and the claims processor 108. Due to network connectivity, various methodologies as described herein may be practiced in the context of distributed computing environments. Although the switch provider 104 is shown for simplicity as being in communication with the pharmacy 102 or claims processor 108 via one intervening network 110, it is to be understood that any other network configuration is possible. For example, intervening network 110 may include a plurality of networks, each with devices such as gateways and routers for providing connectivity between or among networks 110. Instead of or in addition to a network 110, dedicated communication links may be used to connect the various devices in accordance with example embodiment invention. For example, the switch provider 104 may form the basis of network 110 that interconnects the pharmacy 102 and the claims processor 108.

Those of ordinary skill in the art will appreciate that the system 100 shown in and described with respect to FIG. 1 is provided by way of example only. Numerous other operating environments, system architectures, and device configurations are possible. Accordingly, embodiments of the invention should not be construed as being limited to any particular operating environment, system architecture, or device configuration.

Figure 2:
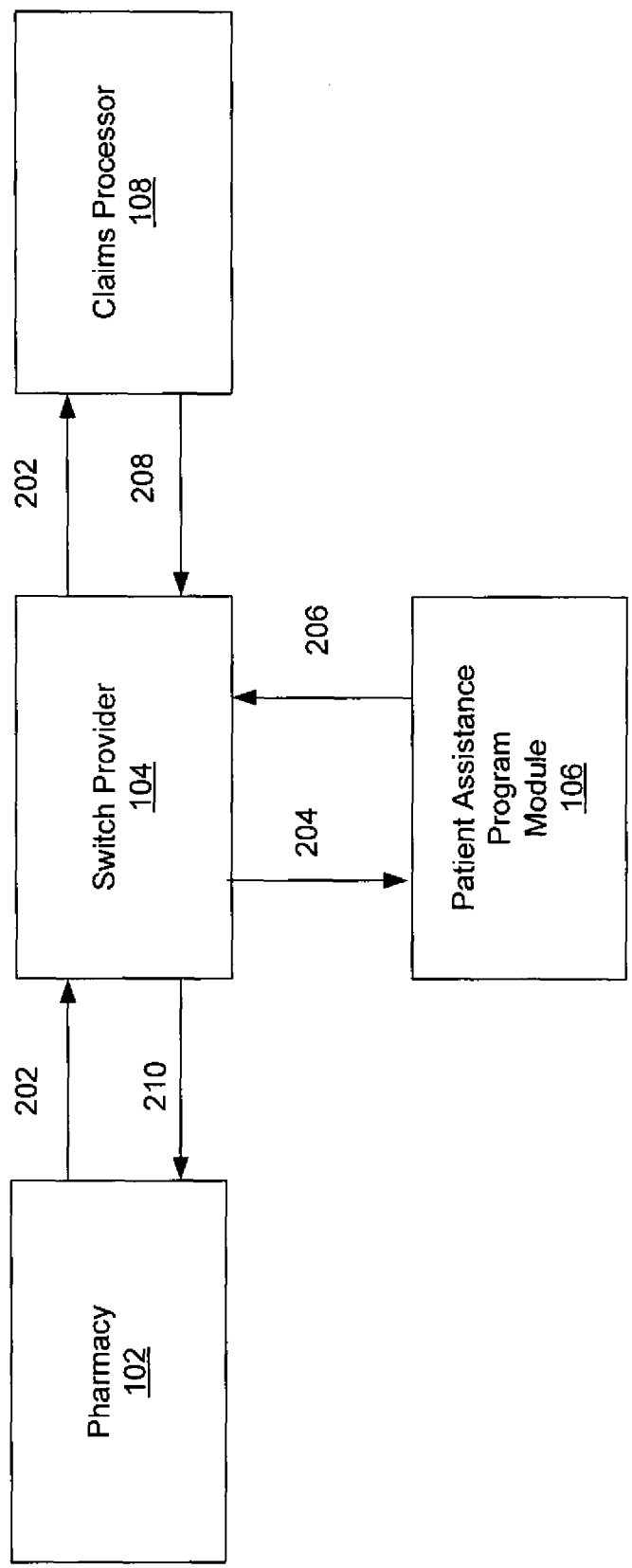
FIG. 2 illustrates an example block diagram of a system for converting denied claim responses to approved claim responses, according to an example embodiment of the invention.
Figure 3:
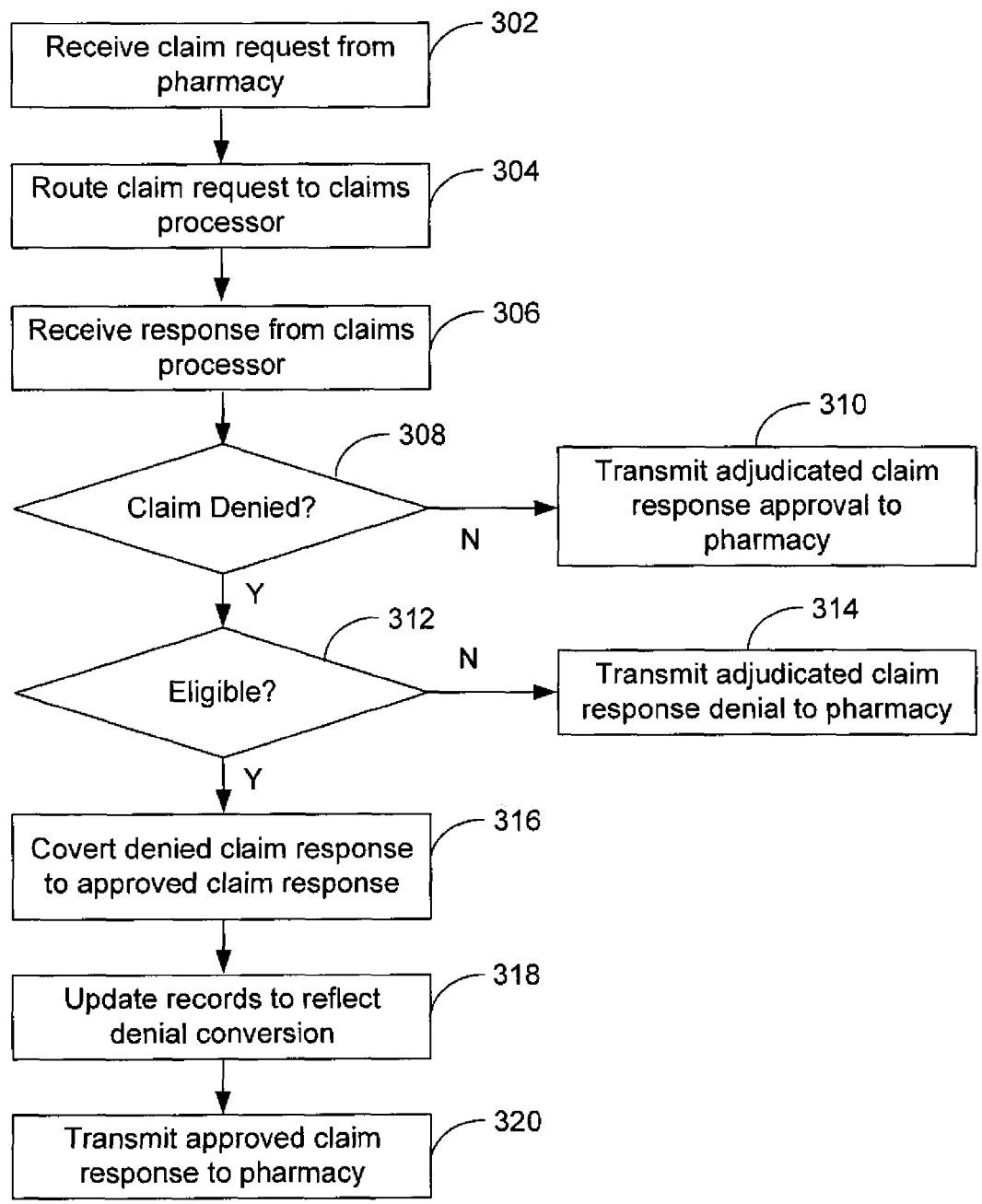
FIG. 3 illustrates an example flow diagram for converting denied claim responses to approved claim responses, according to an example embodiment of the invention.

FIG. 2 illustrates an example block diagram of a system for converting denied claim responses to approved claim responses, according to an example embodiment of the invention. The block diagram of FIG. 2 will be discussed in conjunction with the flow diagram of FIG. 3. Referring now to FIGS. 2 and 3, in block 302, a customer may provide a product order (e.g., prescription drug order, medical equipment order, etc.) that is entered by a user 124 into the pharmacy 102, which is then transmitted to the switch provider 104 in the form of the electronic prescription claim 202. The electronic prescription claim 202 received by the switch provider 104 via network 110 and I/O interface 130 may include one or more of the following information:

an identification of the drug (e.g., National Drug Code (NDC)) or other product (e.g., medical equipment such as a DME product), a quantity of the drug or other product, pricing information for the drug or product (e.g., network price, Usual & Customary price), a date of the claim request, and a pharmacy identification number.

In block 304, the switch provider 104 may route the prescription claim 202, via network 110 and I/O interface 130, to a claims processor 108 for adjudication and processing, such as benefits and/or coverage determination processing. According to an embodiment of the invention, a Banking Identification Number (BIN)/Processor Control Number (PCN) may also be included in the prescription claim 202 to specify which claims processor 108 the prescription claim 202 should be routed to. According to another embodiment of the invention, the switch provider 104 may also utilize a routing table, perhaps stored in memory 128 or data storage device 142, for determining which claims processor 108 the prescription claim 202 should be routed to. As described above, the claims processor 108 may be associated with a third-party payor such as a PBM or insurance company.

In block 306, the switch provider 104 may receive a response 208 to the prescription claim 202 from the claims processor 108, where the response 208 may include the status or results of the benefits and/or coverage determination from the claims processor 108. In block 308, if the response 208 indicates that the claim has not been denied, then the response 208 may be an approved claim response that specifies the covered (e.g., insured) amount and any patient-responsible (e.g., co-pay) amount from the claims processor 108. Processing may then proceed to block 310 with the switch provider 104 transmitting a response 210 in the form of an adjudicated and approved claim to the pharmacy 102 via network 110 and respective I/O interfaces 130, 114. The pharmacy 102 may then know the covered (e.g., insured) amount and any patient-responsible (e.g., co-pay) amount.

On the other hand, block 308 May determine, based upon the response 208 to the prescription claim 202 from the claims processor 108, that the prescription claim 202 has been denied. According to an example embodiment of the invention, a denied claim may result from a claims processor 108 not accepting financial responsibility for any portion of the prescription claim 202. For example, the response 210 for a denied claim may include one of the following denial reasons or reject codes (e.g., NCPDP codes):

(70) Product/Service Not Covered, (AC) Product Not Covered Non-Participating Manufacturer, or

(73) Refills not covered.

It will be appreciated that other reject codes and denial reasons may be utilized without departing from example embodiments of the invention. In this situation, processing may proceed with block 312 determining whether the denied claim is eligible for funding, perhaps by a pharmaceutical manufacturer or another entity. For example, processing for block 312 may include the switch provider 104 providing at least a portion of the received prescription claim 202 in the form of qualification information 204 to the patient assistance program module 106. The qualification information 204 may specify at least the identification of the drug or other product, or yet other information, including pricing information, from one or both of the prescription claim 202 or the response 208. The patient assistance program module 106 may determine whether the identified drug or other product is eligible for funding by a pharmaceutical manufacturer or other entity, and if so, the extent to which funding is available. For example, a particular drug or other product may be associated with a maximum eligible funding amount. The patient assistance program module 106 may then provide a message 206 regarding the availability and amount of funding to the switch provider 104.

Based upon the received message 206 from the patient assistance program module 106, the switch provider 104 may determine that the denied claim is not eligible in block 312 for funding by a pharmaceutical manufacturer or other entity. In this case, a response 210 in the form of a denied claim is transmitted to the pharmacy 102, as illustrated by block 314. On the other hand, in block 312, the switch provider 104 may determine that the denied claim is eligible for funding by a pharmaceutical manufacturer or other entity. In this case, the switch provider 104 may covert the denied claim response to an approved claim response, as illustrated in block 316. The switch provider 104 may also append or insert a message with the approved claim response to communicate the denial conversion to the pharmacy 102. The approved claim response may also include a patient-responsible amount (e.g., a co-pay or co-insurance) if the pharmaceutical manufacturer or other entity does not cover the full amount of the drug or other product. According to an example embodiment of the invention, the switch provider 104 and/or patient assistance program module 106 may also update its financial records to reflect the conversion of a denied claim to an approved claim, as illustrated by block 318. It will be appreciated that these financial records may be utilized for fulfilling payments or other credits to the pharmacy 102, perhaps on a periodic basis (e.g., near realtime, daily, weekly, monthly, etc.). A response 210 in the form of an approved claim, and optionally a message indicating the denial conversion, may then be transmitted from the switch provider 104 to the pharmacy 102, as illustrated in block 320.

It will be appreciated that many variations of FIGS. 2 and 3 are available in accordance with alternate embodiments of the invention. For example, FIGS. 2 and 3 disclose qualification of a funding opportunity as being performed in step 312 after a denied claim has been provided by a claims processor. However, in accordance with an example embodiment of the invention, the determination of a funding opportunity may be initiated at the time the initial claim is received by a switch provider and forwarded to a claims processor. In this way, a switch provider and/or patient assistance program module may prequalify the initial claim while the claims processor adjudicates the claim. Accordingly, once the claims processor denies the claim, the switch provider and/or patient assistance program module would have already begun the process of determining whether the denied claim is eligible for funding, and if so, the extent to which funding is available.

Figure 4:
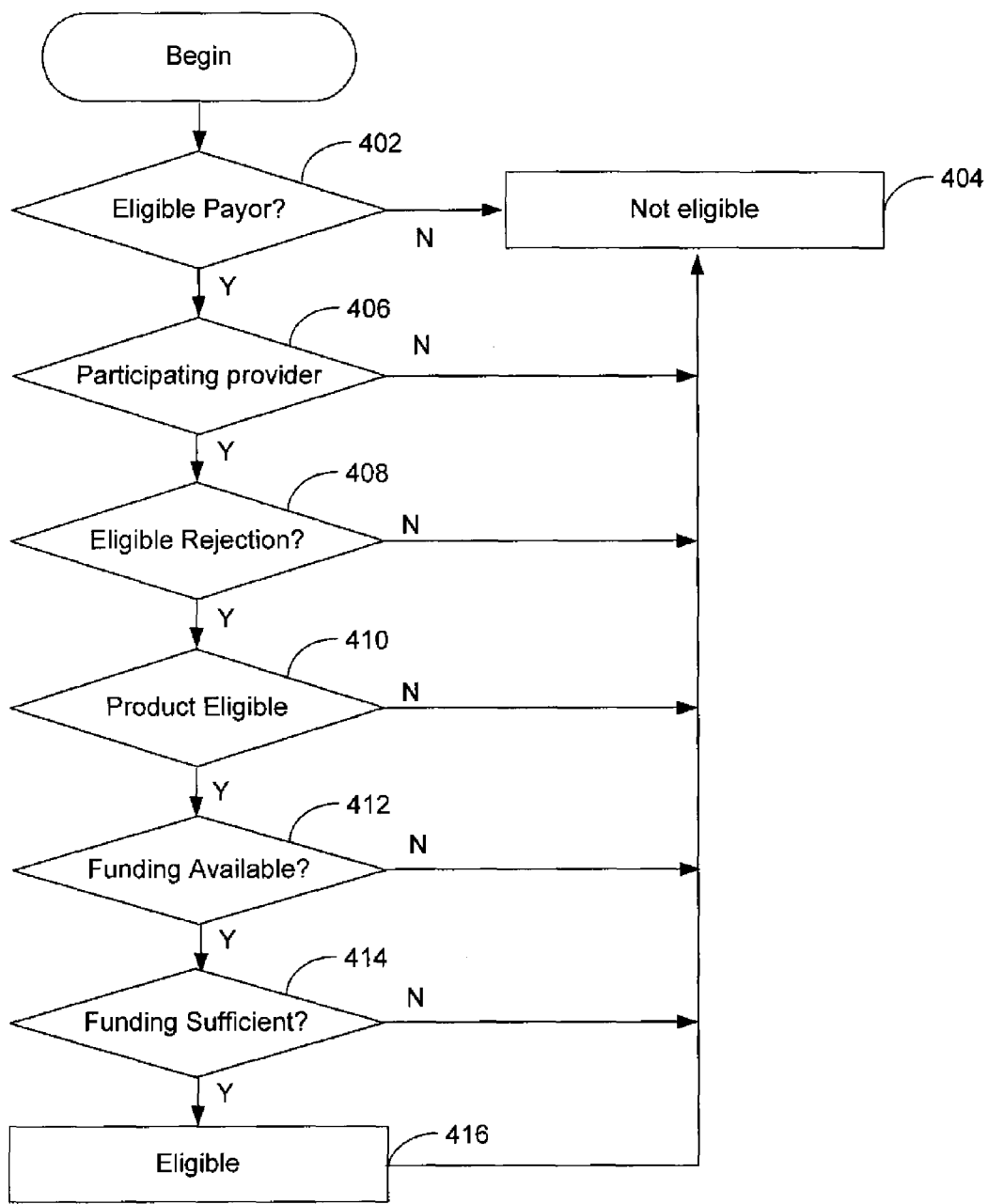
FIG. 4 illustrates a process for determining whether a denied claim request is eligible for funding by a pharmaceutical manufacturer, according to an example embodiment of the invention.

FIG. 4 illustrates a process for determining whether a denied claim may be eligible for funding by a pharmaceutical manufacturer. It will be appreciated that while the process of FIG. 4 may be illustrated as being performed by a patient assistance program module 106, the process could likewise be performed by a switch provider 104, either alone or in conjunction with the patient assistance program module 106.

FIG. 4 begins with block 402 determining whether the claim is directed towards an eligible claims processor 108 and/or payor associated with the claims processor 108. According to an example embodiment of the invention, an eligible payor may be determined based upon a BIN/PCN provided in a claim. For example, the switch provider 104 or a patient assistance program module 106 may include an exception list of BIN/PCNs for ineligible payors. Examples of ineligible payors may include certain government payors or PBMs. If the claim is directed towards an ineligible payor (block 402), then the switch provider 104 and/or patient assistance program module 106 may determine that the claim is not eligible for funding by a pharmaceutical manufacturer or other entity (block 404).

Block 402 may also determine that the claim is not going to an ineligible payor, in which case processing may continue with block 406 determining whether the pharmacy 102 submitting the claim is a participating provider. According to an embodiment of the invention, the switch provider 104 may include a list of National Council for Prescription Drug Programs (NCPDP) numbers and/or national provider identifier (NPI) numbers for determining participating pharmacies 102. If block 406 determines the pharmacy 102 submitting the claim is a non-participating provider, then the switch provider 104 and/or patient assistance program module 106 may determine that the claim is not eligible for funding by a pharmaceutical manufacturer or other entity (block 404). On the other hand, block 406 may determine that the pharmacy 102 submitting the claim is a participating provider, and processing may continue with block 408.

Block 408 determines whether the claim was rejected by the claims processor 108 for a qualified reason. According to an embodiment of the invention, some examples of qualified reasons may include any of the following: (i) product/service not covered (i.e., NCPDP Reject Code "70"), (ii) Product Not Covered Non-Participating Manufacturer (i.e. NCPDP Reject Code "AC"), and (iii) refills are not covered (i.e., NCPDP Reject Code "73"). An example of a non-qualified reason may be the following: (i) M/T Cardholder ID (i.e. NCPDP Reject Code "07"), and (ii) M/I Date of Service (i.e. NCPDP Reject Code "15". If block 408 determines that the claim was not rejected for a qualified reason, then the switch provider 104 and/or patient assistance program module 106 may determine that the claim is not eligible for funding by a pharmaceutical manufacturer or other entity (block 404). On the other hand, if block 408 determines that the claim was rejected for a qualified reason, then processing proceeds to block 410.

Block 410 may determine whether the drug or other product identified in the claim is eligible for funding by a pharmaceutical manufacturer or other entity. According to an embodiment of the invention, the switch provider 104 or patient assistance program module 106 may compare the national drug code (NDC) specified in the claim to its list of eligible NDCs. In alternative embodiments, the switch provider 104 may also identify one or more classes or types of drugs or other products as eligible for funding by a pharmaceutical manufacturer or other entity. If block 410 determines an ineligible drug or other product, then the switch provider 104 and/or patient assistance program module 106 may determine that the claim request is not eligible for funding by a pharmaceutical manufacturer (block 404). On the other hand, if block 410 determines an eligible drug or other product, then processing continues with block 412.

Block 412 may determine whether funds have been made available (or agreed or guaranteed to be made available) by a pharmaceutical manufacturer or other entity for covering a rejected claim request. If block 412 determines that no funds are currently available, then processing may proceed to block 404, wherein the claim request is not eligible for funding by a pharmaceutical manufacturer. On the other hand, if block 412 determines that funds are available, the processing proceeds to block 414.

Block 414 may determine whether the available funds (or agreed or guaranteed funds) are sufficient to cover the amount of the rejected claim, or at least a satisfactory portion of the rejected claim (e.g., an amount that was expected to be covered by the claims processor 108). Block 414 may include comparing the pricing information in the claim request to one or more thresholds to determine how much funds would be required, and perhaps whether they exceed a maximum allowable benefit. If block 414 determines that the funds are not sufficient, the processing proceeds to block 404, wherein the claim request is not eligible for funding by a pharmaceutical manufacturer (block 404). On the other hand, if block 414 determines that the funds are sufficient, the processing proceeds to block 416, where the claim is determined to be eligible for funding by a pharmaceutical manufacturer or other entity.

It will be appreciated that other blocks besides those illustrated in FIG. 4 may be utilized without departing from embodiments of the invention. For example, eligibility may also be based, at least in part, upon the number of prescriptions filled by a patient in a particular amount of time, the length of time that the customer has been using the drug or other product, or the age of the customer. Likewise, not all of the blocks set forth in FIG. 4 may be utilized for an implementation in accordance with an example embodiment of the invention. For example, blocks 402, 406, 408, and 414 may be considered optional, according to an example embodiment of the invention.

An example of funding by a pharmaceutical manufacturer or other entity in accordance with a patient assistance program may now be described in further detail. According to an example embodiment of the invention, a request drug or other product associated with a rejected claim may have a Usual and Customary Charge (U&C) price of $159.99. However, in accordance with the patient assistance program, the network price for the same drug or other product may be $142.75, and since the network price is lower than the U&C price, the patient may be eligible for the lower network price of $142.75. Likewise, in accordance with the patient assistance program, the patient co-pay amount may be determined to be $42.75 with the pharmaceutical manufacturer or other entity funding the remaining $100. In this case, the rejected claim may be converted by the switch provider to an approved claim, wherein the approved claim specifies the $42.75 patient co-pay amount and the $100 manufacturer-funded amount. It will also be appreciated that the pharmaceutical manufacturer or other entity may specify a maximum benefit amount, such as $90 instead of $100. In this case, the patient co-pay amount may need to be increased as necessary, or otherwise, the conversion of the denied claim may not occur, according to an example embodiment of the invention.

According to example embodiment of the invention, a reversal of one or more converted claims may be necessary. With such claim reversals, a pharmacy may submit a prescription claim reversal request specifying a product to the switch provider, and the switch provider may deliver the prescription claim reversal to the patient assistance program module. The patient assistance program module may then determine if the prescription claim reversal is associated with a previously paid "denial conversion" as described herein. If "yes", the patient assistance program module, either alone or in conjunction with another application, may direct a reversal of the previously paid prescription claim. If "no", the switch provider may route the prescription claim reversal request to the claims processor specified by the prescription claim reversal request. A prescription claim reversal request may occur for a fully funded (i.e. 100%) prescription claim or a partially funded (i.e. <100%) prescription claim.

According to another example embodiment of the invention, coordination of benefits prescription claims may likewise be provided by a pharmacy. In particular, a pharmacy may submit a coordination of benefits (COB) prescription claim request for a product to the switch provider, and the switch provider may deliver the COB prescription claim request to the patient assistance program module. The patient assistance program module may then determine if the COB prescription claim is related to a request for a previously paid "denial conversion". If "Yes", and the claims processor for the COB prescription claim is defined as a government funded program, the application denies the request with a message to reverse the original claim. If "No", and the claims processor is defined as a government funded program, then the switch provider may forward the prescription claim request to the identified claims processor.

Many modifications and other embodiments of the invention will come to mind to one skilled in the art to which this invention pertains having the benefit of the teachings presented in the foregoing descriptions and the associated drawings. Therefore, it is to be understood that the invention is not to be limited to the specific embodiments disclosed and that modifications and other embodiments are intended to be included within the scope of the appended claims. Although specific terms are employed herein, they are used in a generic and descriptive sense only and not for purposes of limitation.

That which is claimed:

1. A computer-implemented method for claim denial conversion, comprising:
   receiving, by a switch provider comprising one or more computers, a prescription claim from a pharmacy computer, wherein the prescription claim is associated with a product requested by a customer;
   routing, by the switch provider, the prescription claim to a claims processor for adjudication, the claims processor associated with a third-party payor;
   receiving, by the switch provider from the claims processor, a denied claim response for the claim request, the denied claim response indicating denial of any financial coverage for the prescription claim;
   determining, by the switch provider, that funding is available to cover at least a portion of a price of the requested product;
   converting, by the switch provider, the denied claim response to an approved claim response upon determination of the available funding; and
   transmitting, by the switch provider, the approved claim response to the pharmacy computer, the approved claim response being responsive to the received prescription claim, wherein the denied claim response is not transmitted to the pharmacy computer.

2. The computer-implemented method of claim 1, wherein the available funding entirely covers the price of the requested product, or wherein the available funding covers only a portion of the price of the requested product, thereby leaving a customer-responsible amount.

3. The computer-implemented method of claim 2, wherein the approved claim transmitted to the pharmacy computer includes the customer-responsible amount.

4. The computer-implemented method of claim 1, further storing a financial record associated with the conversion of the denied claim response to the approved claim response, wherein the financial record specifies a payment amount for a pharmacy associated with the pharmacy computer.

5. The computer-implemented method of claim 1, wherein converting the denied claim response to the approved claim response is a denial conversion for the prescription claim, and further comprising:
   receiving, by the switch provider, a coordination of benefits (COB) claim from the pharmacy computer;
   determining, by the switch provider, that the COB claim is related to the denial conversion;
   determining, by the switch provider, that the COB claim is associated with a government funded program; and
   transmitting, by the switch provider, a second denied response for the COB claim to the pharmacy computer, wherein the second denied response includes a message to reverse the denial conversion for the prescription claim.

6. The computer-implemented method of claim 1, wherein the received coverage information indicates that the claim is rejected by the claims processor, and wherein the available discount or payment is associated with complete payment of the claim such that the amount payable by the customer is zero.

7. The computer-implemented method of claim 1, wherein determining that funding is available includes determining one or more of the following: (i) determining an eligible denial reason for denied claim, or (ii) determining that an identifier associated with the requested product is eligible for funding.

8. The computer-implemented method of claim 1, wherein determining that the funding is available includes determining one or more of the following: (i) determining that an eligible claims processor adjudicated the claim, or (ii) determining that the prescription claim is received from an eligible pharmacy.

9. The computer-implemented method of claim 1, wherein the funding is provided by a manufacturer associated with the requested product.

10. The computer-implemented method of claim 1, wherein determining that funding is available to cover at least a portion of a price of the requested product includes transmitting information associated with the prescription claim to a patient assistance program module and receiving a message from a patient assistance program module indicating the available funding.

11. A system for claim denial conversion, comprising:
at least one memory of a switch provider configured to store computer-executable instructions;
at least one computer processor of the switch provider in communication with the at least one memory, wherein the at least one computer processor of the switch provider is operable to execute the computer-executable instructions to:
receive a prescription claim from a pharmacy computer, wherein the prescription claim is associated with a product requested by a customer,
route the prescription claim to a claims processor for adjudication, the claims processor associated with a third-party payor,
receive, from the claims processor, a denied claim response for the claim request, the denied claim response indicating denial of any financial coverage for the prescription claim,
determine that funding is available to cover at least a portion of a price of the requested product,
convert the denied claim response to an approved claim response upon determination of the available funding, and
transmit the approved claim to the pharmacy computer, the approved claim response being responsive to the received prescription claim, wherein the denied claim response is not transmitted to the pharmacy computer.

12. The system of claim 11, wherein the available funding entirely covers the price of the requested product, or wherein the available funding covers only a portion of the price of the requested product, thereby leaving a customer-responsible amount.

13. The system of claim 12, wherein the approved claim transmitted to the pharmacy computer includes the customer-responsible amount.

14. The system of claim 11, wherein the processor is further operable to execute the computer-executable instructions to store in the memory a financial record associated with the conversion of the denied claim response to the approved claim response, wherein the financial record specifies a payment amount for a pharmacy associated with the pharmacy computer.

15. The system of claim 11, wherein the conversion of the denied claim response to the approved claim response is a denial conversion for the prescription claim, and wherein the processor is further operable to execute the computer-executable instructions to:
receive a coordination of benefits (COB) claim from the pharmacy computer;
determine that the COB claim is related to the denial conversion;
determine that the COB claim is associated with a government funded program; and
transmit a second denied response for the COB claim to the pharmacy computer, wherein the second denied response includes a message to reverse the denial conversion for the prescription claim.

16. The system of claim 11, wherein the received coverage information indicates that the claim is rejected by the claims processor, and wherein the available discount or payment is associated with complete payment of the claim such that the amount payable by the customer is zero.

17. The system of claim 11, wherein the processor is operable to execute the computer-executable instructions to determine that funding is available by (i) determining an eligible denial reason for denied claim, or (ii) determining that an identifier associated with the requested product is eligible for funding.

18. The system of claim 11, wherein the processor is operable to execute the computer-executable instructions to determine that funding is available by (i) determining that an eligible claims processor adjudicated the claim, or (ii) determining that the prescription claim is received from an eligible pharmacy.

19. The system of claim 11, wherein the funding is provided by a manufacturer associated with the requested product.

20. The system of claim 11, wherein the processor is operable to execute the computer-executable instructions to determine that funding is available by transmitting information associated with the prescription claim to a patient assistance program module and receiving a message from a patient assistance program module indicating the available funding.

* * * * *